United States Patent [19]

Nomura et al.

[11] Patent Number: 4,941,939
[45] Date of Patent: Jul. 17, 1990

[54] APPARATUS FOR APPLYING AN ELASTIC BAND ONTO A MOVING WEB

[75] Inventors: Hironori Nomura, Iyomishima; Taiji Shimakawa, Kawanoe; Junji Shinohara, Iyomishima; Shigetoyo Kobayashi, Kagawa; Hiroki Yamamoto, Kawanoe, all of Japan

[73] Assignee: Uni-Charm Corporation, Ehime, Japan

[21] Appl. No.: 291,645

[22] Filed: Feb. 28, 1989

Related U.S. Application Data

[62] Division of Ser. No. 215,359, Jul. 5, 1988, Pat. No. 4,838,969.

[30] Foreign Application Priority Data

Jul. 3, 1987 [JP] Japan .................................. 62-166523

[51] Int. Cl.$^5$ ............................................. B32B 31/16
[52] U.S. Cl. .................... 156/495; 156/494; 156/160; 156/163; 156/164; 604/358
[58] Field of Search ................ 156/177, 160, 161–164, 156/204, 227, 176, 178, 229, 201, 494, 495, 303, 299, 209, 459, 464, 470, 471; 604/358, 373, 385.1, 385.2

[56] References Cited

U.S. PATENT DOCUMENTS

| 4,246,900 | 1/1981 | Schroder ...................... 604/385.2 X |
| 4,293,367 | 10/1981 | Klasek et al. ........................ 156/494 |
| 4,300,967 | 11/1981 | Sigl ....................................... 156/164 |
| 4,430,086 | 2/1984 | Repke ............................... 604/285.2 |
| 4,479,836 | 10/1984 | Dickover et al. .............. 156/229 X |
| 4,578,133 | 3/1986 | Oshefsky et al. .................... 156/164 |
| 4,618,384 | 10/1986 | Sabee ................................... 156/205 |
| 4,661,102 | 4/1987 | Shikata et al. ................... 604/385.2 |
| 4,675,068 | 6/1987 | Lundmark ...................... 156/164 X |

Primary Examiner—Michael W. Ball
Assistant Examiner—Jeff H. Aftergut
Attorney, Agent, or Firm—Fred Philpitt

[57] ABSTRACT

A moving web is folded at its predetermined length at its opposite side portions so that the opposite side portions are opposed to each other at a predetermined angle with its central portion. Then part of each of the opposite folded portions is outwardly folded. These foldings occur so that a first folding line and a second folding line being opposed to each other at each side of the web include portions in non-parallel relationship. Elastic bands are affixed onto the web along the second opposite folded portions longitudinally and substantially in parallel to each other. When the web is flattened from the folded condition, the paired elastic band affixed onto the web at its opposite sides each has a diagonal orientation symmetrically with respect to the direction in which the web moves.

7 Claims, 6 Drawing Sheets

APPARATUS FOR APPLYING AN ELASTIC BAND ONTO A MOVING WEB

This is a division of application Ser. No. 215,359 filed July 5, 1988 now U.S. Pat. No. 4,888,969.

BACKGROUND OF THE INVENTION

The present invention relates a method and an apparatus to affix longitudinally an elastic band pair onto a moving web as a primary component of continuous article along opposite sides of a said web so that said elastic band pair may be disposed on the web at least partially in a non-parallel relationship to each other.

The present invention is applicable to the production of disposable articles placed on the crotch area of the human body and provided with elastic band to assure fitness around the legs, for example, a diaper, diaper cover or training pants for babies, to thereby affix said elastic bands onto such article on opposite sides of the crotch area in a diagonal, curved or non-parallel disposition.

To obtain the desired fitness around the legs of user and thereby to minimize possible leakage of excretions, for example, in a disposable diaper or pants, there have already been proposed methods and the apparatuses for affixing the elastic band onto such article on opposite sides of the crotch area in a diagonal or curved, i.e., non-parallel disposition.

In such prior art, the inventive concepts have been often involved into the means to feed the elastic band to a moving web as the primary component of the continuous article and to affix this elastic band onto the web.

However, to construct said means so that the elastic band can be affixed onto the web in a non-parallel disposition, for example, diagonal or curved disposition, the mechanism of such means is necessarily complicated and it is difficult for such a complicated mechanism to be continuously operated at a high speed so that the elastic band may be affixed, through the entire length of the web, at predetermined positions in orderly and uniform manner. In view of such difficulties, the elastic band has usually been affixed onto the disposable diaper at opposite sides of the crotch area, regardless of the teachings of prior art. It will be readily appreciated that diaper provided with the elastic band in such a parallel disposition can not provide satisfactory fitness around the legs of user. This not only deteriorates appearance and feeling but also may permit leakage of excretions.

The object of this invention is to overcome the problems as set forth above with a relatively simple method and apparatus.

THE INVENTION

The above-mentioned object is achieved by a method and apparatus for continuously feeding web as a primary component of the continuous article to a process to combine said web with longitudinally elastic band and for affixing said elastic band onto said web, respectively as follows:

Method comprising steps of:

at said process of combination, folding (first folding) a predetermined length of said (web at least corresponding to a single individual article) at opposite side portions thereof so that said opposite side portions are opposed to each other at a predetermined angle with a central portion of said web and then partially folding- (second folding) each of said opposite folded portions outwardly, these foldings occurring so that a first folding line and a second folding line being opposed to each other at each side of said web include portions in non-parallel relationship; and said folding defines a deformation of the web out of the plane of that web affixing the elastic band onto said web along a portion defined between said second folding line and the outermost edge at each side of said web, parallel to the longitudinal divertion of said web, longitudinally and substantially in parallel to the elastic band on the other side of said web; and flattening said web from said folded condition so as to achieve a desired final disposition of said elastic band that said elastic band affixed onto said web at opposite sides thereof each has a diagonal orientation symmetrically with respect to the direction in which said web travels.

Apparatus comprising:

a support having unevenly contoured peripheral segments in conformity with which said web is folded and curved, each of said unevenly contoured peripheral segments including a grooved central area defining a slope area gradually rising from at least one end of a segment middle portion to the other end in the same direction as said web travels, rising edge areas formed along opposite sides of said grooved central area, and a rising end area continuous with the highest end of said slope area and having substantially same height as that of said rising edge areas; and means to affix paired elastic band substantially in parallel to each other onto said web at portions thereof lying immediately on said opposite rising edge areas while said web is pressed against and folded in conformity with said unevenly contoured peripheral segment.

Apparatus comprising:

a support having unevenly contoured peripheral segments in conformity with which said web is folded and curved, each of said unevenly contoured peripheral segments including a rising central area defining a slope area gradually falling from at least one end of a segment middle portion to the other end in the same direction as said web travels, stepped down edge areas formed along opposite sides of said rising central area, and a falling end area continuous with the lowest end of said slope area and having substantially same height as that of said stepped down edge area; and means to affix paired said elastic band substantially in parallel to each other onto said web at portions thereof lying immediately on said opposite stepped down edge areas while said web is pressed against and folded in conformity with said unevenly contoured peripheral segment.

According to the method of this invention, as will be apparent from the aforegoing description, the opposite sides of the web are folded along the desired lengths thereof so as to form first and second folding lines, said first folding lines and said second folding lines being partially in non-parallel relationship, and the paired elastic bands are fed and affixed onto the web at the top surfaces of the opposite edges corresponding to the opposite second folded portions substantially in parallel relationship to each other so that said paired elastic band may be disposed in non-parallel relationship, (i.e., symmetrically diagonal) when said web is flattened from said folded condition. This unique feature advantageously eliminates the need for the elastic band feeding/holding device, for example, to have a complicated mechanism for the deflection of said elastic band and enables the paired elastic band to be continuously fed and affixed in parallel relationship onto the web, although the final result is that said paired elastic band will be disposed on said web in a non-parallel relationship.

According to the apparatus of this invention, on the other hand, the unevenly contoured segments in conformity with which said web is folded and curved are formed along the supporting periphery of the support for this web. This unique feature advantageously simplifies a mechanism to dispose said paired elastic band on said web, eliminates possibility of troubles and malfunctions, and enables both the web and the elastic band to be operated at a high speed.

PREFERRED EMBODIMENTS OF THE INVENTION

The invention will be described more in detail, by way of example, with reference to the accompanying drawing.

Referring to FIGS. 1 through 4, there is shown an a apparatus for execution of a method according to the invention. The apparatus comprises a circular support 1 that is rotatable around a central axis 0. The support 1 has at predetermined intervals along its periphery grooved central areas 3, rising edge areas 2 provided on opposite sides of the respective grooved central areas 3 and having their inner walls extending substantially in parallel with each other and substantially in perpendicularity to top surfaces of the associated grooved central areas, and relatively shallow grooved areas 4 extending between the adjacent grooved central areas 3 and presenting circular arcs each defined by a radius slightly shorter (or lower) than that of said rising edge areas 2. It should be understood here that such shallow grooved areas 4 may present their circular arcs defined by the same radius as that of said rising edge areas 2 and these areas 4 will be referred to hereinafter as rising end areas 4. Each of said grooved central areas 3 has slope areas 6 gradually rising from a longitudinally middle position 5 of the segment towards opposite rising end areas 4.

Figure 1:
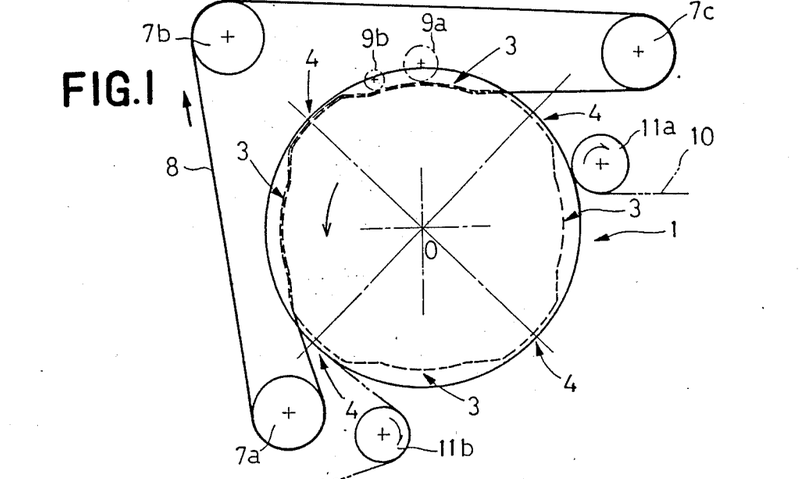
FIG. 1 is a side view schematically showing a rotatable support as an apparatus of the invention used to execute a method of the invention.
Figure 2:
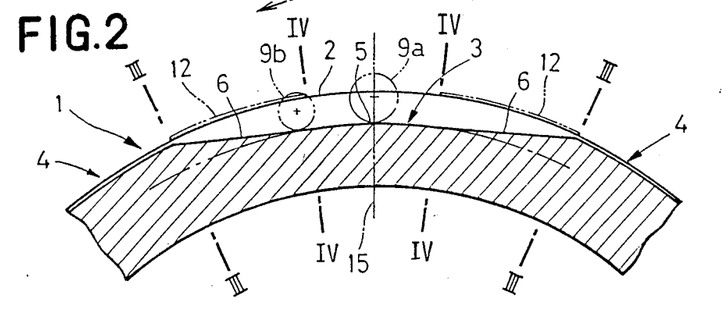
FIG. 2 is a fragmentary sectional view showing a part of said apparatus.
Figure 3:
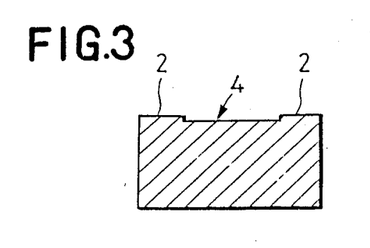
FIG. 3 shows an unevenly contoured peripheral segment of said support in a cross-section taken along a line III—III in FIG. 2.
Figure 4:
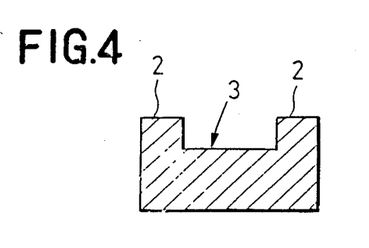
FIG. 4 shows said unevenly contoured peripheral segment in a cross-section taken along a line IV—IV in FIG. 2.

Closely around the support 1, having along its outer periphery unevenly contoured peripheral the aforementioned segments, there are provided three guide rollers 7a, 7b, 7c to guide a press-down belt 8 so that said belt 8 will be against the outer periphery of said support 1 as said belt 8 travels in synchronization with said support. There are provided pressure rollers 9a, 9b in opposition to the top surface of the grooved central area 3 in order to urge the belt 8 against said top surface and these rollers are supported by suitable means with the interposition of springs, respectively, so that said rollers may smoothly follow both said grooved central area 3 and said rising end areas 4 regardless of a difference in heights of these areas. Closely around the support 1, there are additionally provided guide rollers 11a, 11b, and guide roller 11a being adapted to feed web 10 as the primary constituting member of the continuous article, and said guide roller 11b being adapted to take said web 10 out from the support.

Figures 5, 6:
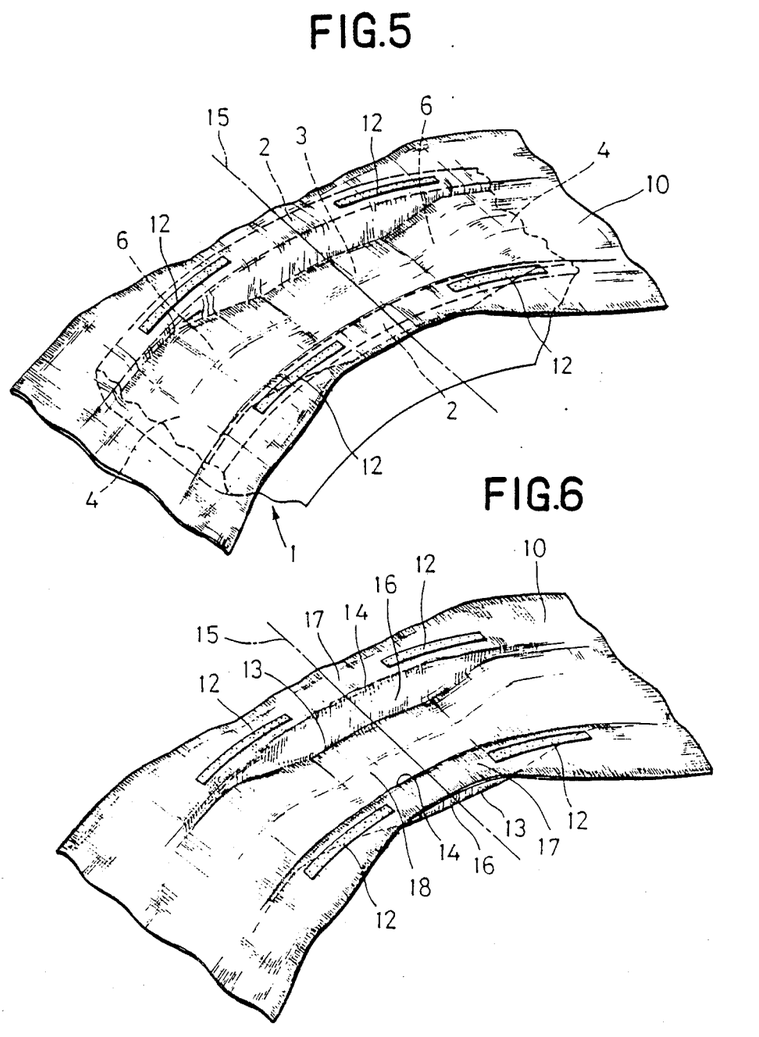
FIG. 5 is a fragmentary perspective view showing web as pressed against and thereby shaped in conformity with said unevenly contoured peripheral segment.
FIG. 6 is a view similar to FIG. 5, showing said web after shaped and having pieces of elastic band affixed thereonto.

As shown in FIGS. 1, 2 and 5, the web 10 is fed to the outer periphery of the support 1 which is rotating in a direction as indicated by an arrow and the pressure rollers 9a, 9b cause the belt 8 travelling in a direction as indicated by an arrow to press said web 10 against the grooved central area 3 and the associated rising end areas 4 so that said web 10 is folded and curved in conformity with these areas.

There is provided above or laterally of the opposite rising edge areas 2, though not shown, a device operating synchronously with the support 1 to cut a continuous elastic band (not shown), stretched and applied with suitable adhesive into pieces of predetermined length, and to feed each of these cut pieces intermittently onto the web 10. Particular types of this device are not critical so long as the device functions in the manner mentioned above and it may be of the prior art. This device enables the pieces of elastic band 12 to be affixed onto the web 10. substantially in a parallel relationship with each other along the tops of said opposite rising edge areas 2 which extend along opposite sides of the respective slope areas 6.

Figure 7:
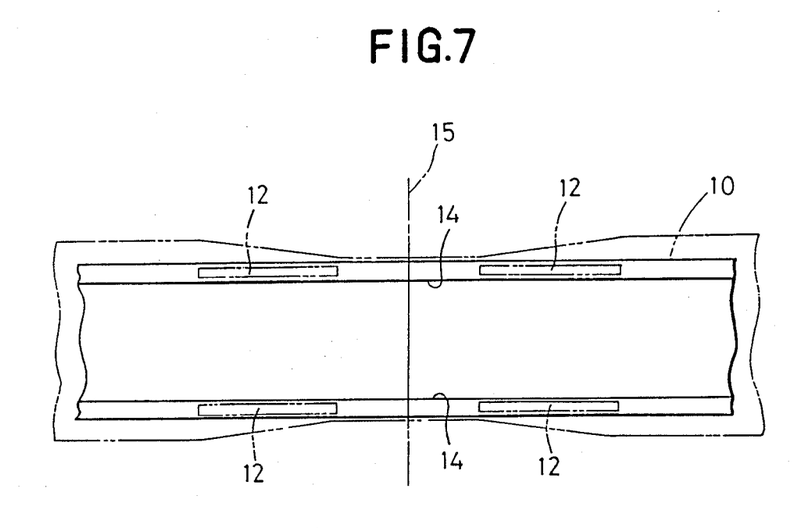
FIG. 7 is a plan view showing said web after shaped and having pieces of elastic band affixed thereonto.
Figure 8:
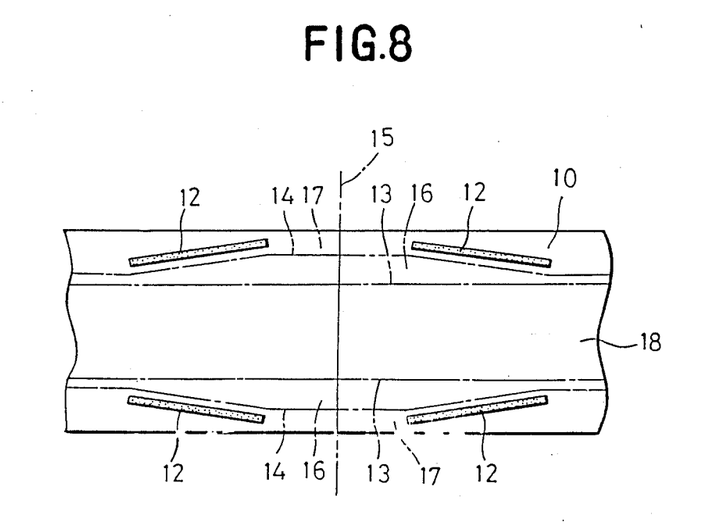
FIG. 8 is a view similar to FIG. 7, showing said web after shaped and having pieces of elastic band affixed thereonto, but as having been flattened.

As seen in FIGS. 6 and 7, in a section of the web 10 that has been shaped and provided with the pieces of elastic band 12 affixed thereonto, opposite first folding lines 13 as well as opposite second folding lines 14 extend substantially in parallel to each other, respectively, and respective first folded portions 16 are substantially perpendicular to a central portion 18 and respective second folded portions 17 are substantially perpendicular to said first folded portions 16. However, when this central section of the web 10 is flattened, the opposite second folding lines 14 are moved out of the parallel relationship and, accordingly, the opposite pieces of elastic band 12 become disposed in a non-parallel pattern as shown by FIG. 8. Such pattern of the elastic band pieces 12 will be repeated longitudinally of the web 10 and, once the continuous article has been completed, the web 10 will be cut along a middle line 15 between each pair of the longitudinally adjacent patterns of the elastic band pieces 12 into individual articles.

As has previously been mentioned, the pieces of elastic band 12 are intermittently affixed onto the web 10 in this embodiment. However, it is also possible for the continuous elastic band 12 to be intermittently applied with adhesive leaving portions which are not affixed onto the web 10, then said continuous elastic band 12 is affixed at said portions applied with adhesive onto the web 10 and cut at said portions having no adhesive so that these portions contract upon said cutting.

Figure 9:
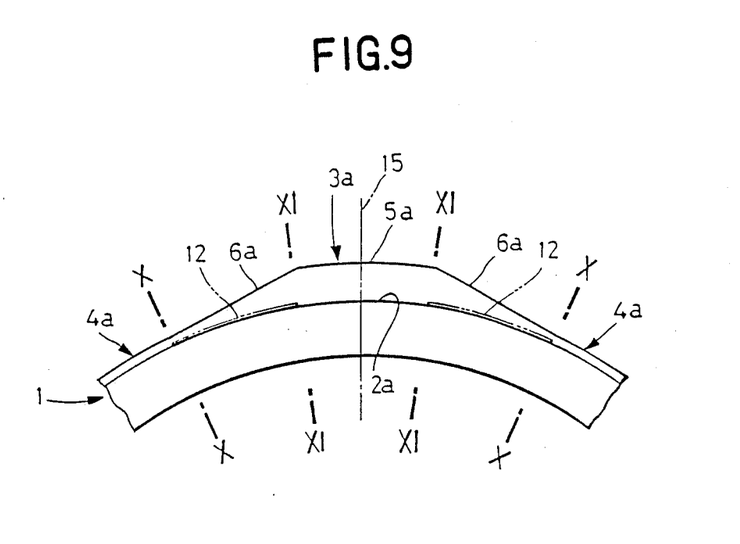
FIG. 9 is a side view partially showing another embodiment of the rotatable support.
Figure 10:
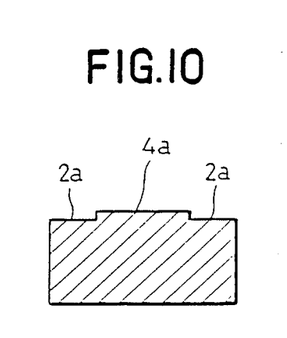
FIG. 10 shows an unevenly contoured peripheral segment of said rotatable support in a cross-section taken along a line X—X in FIG. 9.
Figure 11:
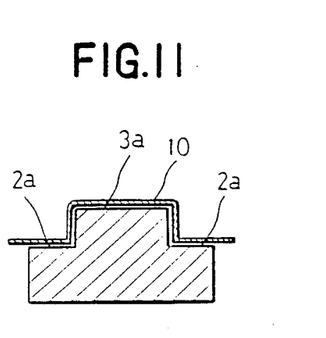
FIG. 11 shows said unevenly contoured peripheral segment in a cross-section taken along a line XI—XI in FIG. 9.

FIGS. 9 through 11 show another embodiment in which the circular rotatable support 1 has along its outer periphery unevenly contoured peripheral segments each basically presenting a configuration that is reverse to that in the support 1 shown by FIGS. 1 through 4. More specifically, this support 1 of FIGS. 9 through 11 has a rising central area 3a, stepped down edge areas 2a and grooved end areas 4a at positions corresponding to said grooved central area 3, said rising edge areas 2 and said rising end areas 4, respectively, of the previous embodiment. The rising central area 3a gradually falls from a segment middle area 5a towards the opposite grooved end areas 4a, forming respective slope areas 6a. The web 10 is pressed against the outer periphery of this support 1 so as to shape respective portions of the web 10 in conformity with the respective unevenly contoured peripheral segments of the support 1 and pieces of elastic band 12 are affixed onto the web 10 substantially in parallel to each other along the portions of the opposite grooved edge areas 2a that extend along opposite sides of the respective slope areas 6a. The pieces of elastic, band 12 will form the pattern as shown by FIG. 8 when the web 10 is flattened.

Figure 12:
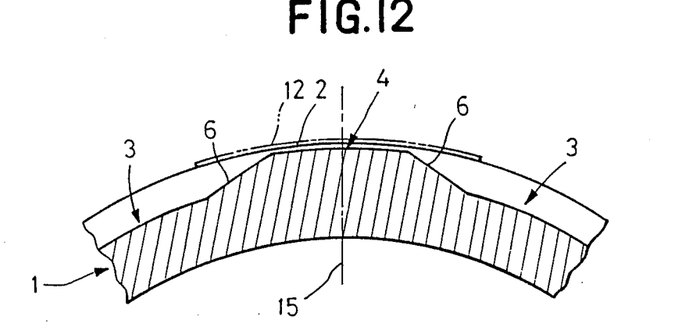
FIG. 12 is a sectional view illustrating an embodiment of the method according to the present invention wherein the unevenly contoured peripheral segements of the support, one of which is shown by FIGS. 1 and 2 are utilized but the pieces of elastic band are affixed onto the web at positions different from those as in FIG. 2.
Figure 13:
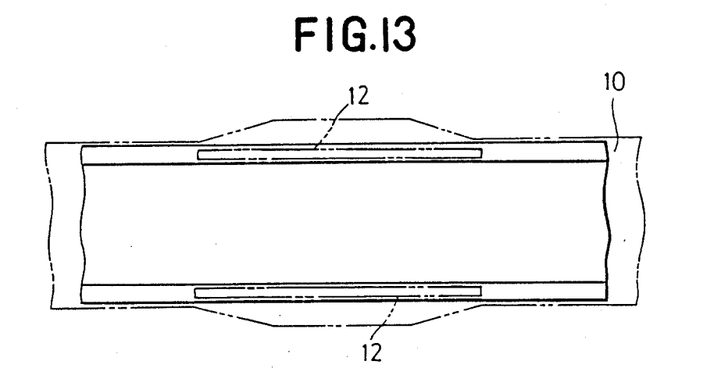
FIG. 13 is a plan view showing the web after pressed against, thereby shaped in conformity with said unevenly contoured peripheral segments one of which is shown by FIG. 12, and then having the pieces of elastic band affixed thereonto.
Figure 14:
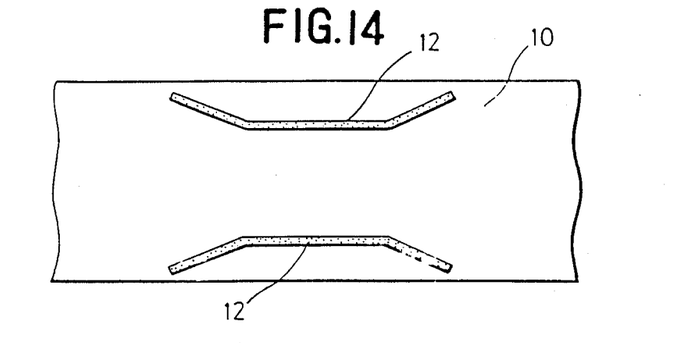
FIG. 14 is a view similar to FIG. 13, showing said web thus press-shaped and having the pieces of elastic band thereonto, but as having been flattened.

FIGS. 12 through 14 show an embodiment in which the support 1 of FIGS. 1 through 4 is utilized but the pieces of elastic band 12 are affixed onto the web 10 in a pattern different from that shown by FIG. 8. According to this embodiment, the pieces of elastic band 12 are affixed substantially in parallel relationship onto the web 10 along portions thereof lying on each rising end area 4 and the opposite rising edge areas 2 extending along opposite sides of the slope areas 6 extending to and from this rising end area 4. When the web 10 is flattened, the pieces of elastic band 12 form a pattern in which the bow-shaped pieces of elastic band 12 are disposed in non-parallel relationship. According to this embodiment, instead of disposing the pieces of elastic band 12 for each pair of individual articles on said portion of the web 10 as shown in FIGS. 2, 5 and 6, the pieces of elastic band 12 for a single individual article are disposed on said portion of the web 10. Accordingly, circumferential lengths of the grooved central area 3 and each rising end area 4 in this support 1 should be shorter than those in the support 1 of FIGS. 1 through 4.

Figure 15:
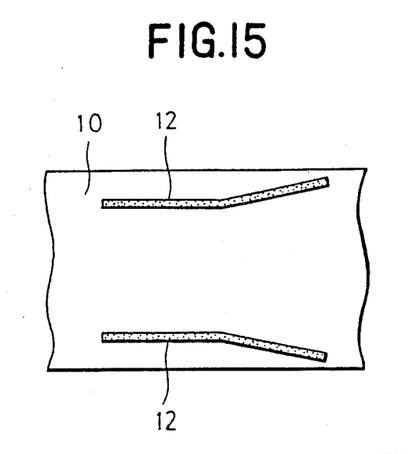
FIG. 15 and 16 are plan views illustrating another embodiment of the method according to the present invention wherein a configuration of said unevenly contoured peripheral segment and/or positions at which the pieces of elastic band are affixed onto the web may be varied to position the pieces of elastic band in a correspondingly varied pattern.
Figure 16:
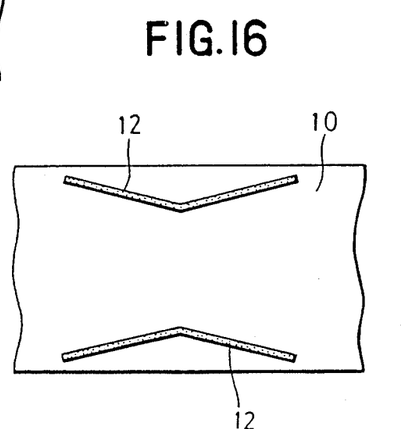

As will be readily understood from the foregoing description, configuration of the unevenly contoured peripheral segments and/or positions at which the elastic band pieces 12 are affixed onto the folded and curved web 10 may be selected to vary a non-parallel disposition of said elastic band pieces 12 on opposite sides of the flattened web 10, for example, as shown by FIGS. 15 and 16.

Although the circular rotatable support 1 having along its outer periphery the unevenly contoured segments in conformity with which the web 10 is folded and curved has been described above particularly with respect to two preferred embodiments, the object of the present invention can be also achieved by a circular arcshaped or a plate-like support which is preferably movable in the same direction as the web 10 travels in synchronization with said web 10, but may be stationary.

What is claimed is:

1. An apparatus for combining a web as a primary component with at least two longitudinal elastic bands so as to affix the elastic bands onto said web in a spaced apart relationship, said apparatus comprising:
   (A) a generally circular main support member (1),
   (B) a plurality of unevenly contoured segments located around the periphery of said support member (1), each of said contoured segments being composed of a central area (3) that includes:
      (a) a middle portion (5),
      (b) sloping areas (6) extending from opposite ends of said middle portion (5) to end areas (4), and
      (c) vertical edge areas (2) formed along opposite sides of said central area (3),
   (C) means (8) to press a web (10) against said plurality of contoured segments, and
   (D) means to affix pairs of elastic bands substantially in parallel to each other onto said web at those portions of the web which extend outwardly from said edge areas (2) while said web is being pressed against and folded in conformity with said unevenly contoured peripheral segment.

2. An apparatus for continuously feeding web as a primary component of continuous article to a process to combine said web with longitudinally elastic band and for affixing said elastic band onto said web, said apparatus comprising;
   a support having unevenly contoured peripheral segments in conformity with which said web is folded and curved, each of said unevenly contoured peripheral segments including a grooved central area defining a slope area gradually rising from at least one end of a segment middle portion to the other end in the same direction as said web travels, rising edge areas formed along opposite sides of said grooved central area, and rising end area continuous with the highest end of said slope area and having substantially same height as that of said rising edge areas; and
   means to affix paired elastic band substantially in parallel to each other onto said web at portions thereof lying immediately on said opposite rising edge areas while said web is pressed against and folded in conformity with said unevenly contoured peripheral segment.

3. An apparatus as recited in claim 2, wherein said opposite rising edge areas have respective inner walls substantially in parallel to each other and substantially perpendicular to the top surface of said grooved central area.

4. An apparatus as recited in claim 2, wherein said support comprises a circular rotatable member adapted to be rotated synchronously with said web in the same direction as said web travels and said rotatable member has along its outer periphery a plurality of said unevenly contoured peripheral segments.

5. An apparatus for continuously feeding web as a primary component of continuous article to a process to combine said web with longitudinally elastic band and for affixing said elastic band onto said web, said apparatus comprising:

a support having unevenly contoured peripheral segments in conformity with which said web is folded and curved, each of said unevenly contoured peripheral segments including a rising central area defining a slope area gradually falling from at least one end of a segment middle portion to the other end in the same direction as said web travels, stepped down edge areas formed along opposite sides of said rising central area, and falling end area continuous with the lowest end of said slope area and having substantially same height as that of said stepped down edge areas; and means to affix paired said elastic band substantially in parallel to each other onto said web at portions thereof lying immediately on said opposite stepped down edge areas while said web is pressed against and folded in conformity with said unevenly contoured peripheral segment.

6. An apparatus as recited in claim 5, wherein opposite outer walls of said rising central area are substantially in parallel to each other and substantially perpendicular to the top surface of said rising central area.

7. An apparatus as recited in claim 5, wherein said support comprises a circular rotatable member adapted to be rotated synchronously with said web in the same direction as said web travels and said rotatable member has along its outer periphery a plurality of said unevenly contoured peripheral segments.

* * * * *